United States Patent [19]

Broger

[11] 4,246,204
[45] Jan. 20, 1981

[54] PROCESS FOR MANUFACTURING TRIPHENYLPHOSPHINE

[75] Inventor: Emil A. Broger, Magden, Switzerland

[73] Assignee: Hoffmann-La Roche Inc., Nutley, N.J.

[21] Appl. No.: 41,216

[22] Filed: May 21, 1979

[30] Foreign Application Priority Data

Jun. 2, 1978 [CH] Switzerland .......................... 6072/78

[51] Int. Cl.³ ................................................ C07F 9/50
[52] U.S. Cl. .................................................... 568/17
[58] Field of Search .................................. 260/606.5 P

[56] References Cited

U.S. PATENT DOCUMENTS 3,405,180  10/1968  Natoli .............................. 260/606.5 P
3,481,988  12/1969  Wünsch et al. ................ 260/606.5 P

OTHER PUBLICATIONS

Masaki et al., Angew. Chem. 89 558 (1977).
Translation Kokai No. 34725 (1978) Mar. 31, 1978.
Wünsch et al., L. Anong. Allg. Chemie, 369 33–37 (1969).

*Primary Examiner*—Helen M. S. Sneed
*Attorney, Agent, or Firm*—Jon S. Saxe; Bernard S. Leon; George W. Johnston

[57] ABSTRACT

A process is disclosed for producing triphenylphosphine by hydrogenating triphenylphosphine dichloride in an inert solvent in the presence of a platinum, palladium, rhodium, ruthenium and/or iridium catalyst.

18 Claims, No Drawings

PROCESS FOR MANUFACTURING TRIPHENYLPHOSPHINE

BACKGROUND OF THE INVENTION

1. Field of the Invention

This invention relates to triphenylphosphine which is a useful reagent in polyene synthesis. 2. Description of the Prior Art Triphenylphosphine can be recovered by the regeneration of triphenylphosphine oxide resulting from a polyene synthesis.

In a prior art process for recovering triphenylphosphine, triphenylphosphine oxide was chlorinated (e.g., by means of phosgene) to give triphenylphosphine dichloride. The latter compound was hydrogenated to yield triphenylphosphine. The hydrogenation of triphenylphosphine dichloride has hitherto been carried out, for example, with hydrogen under pressure (Angew. Chem. 89, 558 1977).

It has now been found that the hydrogenation of triphenylphosphine dichloride can be carried out in a very simple and advantageous manner with hydrogen in the presence of certain catalysts.

SUMMARY OF THE INVENTION

The invention describes a process for producing triphenylphosphine. This compound is a useful reagent in polyene synthesis and can be recovered by the regeneration of triphenylphosphine oxide.

In accordance with the invention, triphenylphosphine dichloride is hydrogenated in an inert solvent in the presence of a platinum, palladium, rhodium, ruthenium and/or iridium catalyst.

DETAILED DESCRIPTION OF THE INVENTION

This invention concerns a process for producing triphenylphosphine.

In accordance with the invention, triphenylphosphine dichloride is hydrogenolyzed in an inert solvent with hydrogen in the presence of a catalyst selected from the group consisting of platinum, palladium, rhodium, ruthenium and iridium.

As used herein, alkoxy connotes alkoxy groups of 1–20 carbon atoms, (e.g., methoxy, ethoxy, isopropoxy, hexoxy). Dioxane is 1,4-diethylene dioxide. Halide denotes flouride, chloride, bromide and iodide.

In a preferred embodiment, triphenylphosphine dichloride is hydrogenated in an inert solvent in the presence of catalytic amounts of platinum, palladium, rhodium, ruthenium and iridium.

The catalyst may consist of one or more of the above named metals either in metallic form or in the form of a metal compound, e.g. a halide. If desired, catalyst carriers, for example carbon, aluminium oxide, silicon dioxide or the like can be used.

The catalyst can be used in catalytic amounts, e.g. in amounts up to about 5% by weight, however, the use of larger amounts is not critical.

The hydrogenation is conveniently carried out at atmospheric pressure, however higher pressures of up to about 100 bar can also be used.

The temperatures used in the hydrogenation depend on the stability of the solvent and may, for example, lie between about 30° and about 130° C. The preferred temperature is from about 50° to about 60° C.

Where the temperatures and pressures used are at the lower end of the noted ranges, the solvent used may conveniently be an ether containing at least two oxygen atoms. Preferably dioxane, or a 1,2-dialkoxyethane, such as 1,2-dimethoxyethane is utilized as the solvent.

Where higher temperatures and pressures are used, other solvents which may also be used include for example, chloroform, benzene, toluene, xylene, cyclohexane and ethyl acetate.

The triphenylphosphine dichloride used as the starting material of the inventive process preferably is free from any chlorinating agent such as phosgene, used in its preparation. The triphenylphosphine dichloride may also be employed in the form of its chloroform adduct of the formula $[(C_6H_5)_3PCl_2 \cdot CHCl_3]$.

The triphenylphosphine dichloride-chloroform adduct can be prepared by any conventional techniques and procedures. Illustratively, triphenylphosphine oxide is chlorinated with phosgene in chloroform to form said adduct.

The process in accordance with the invention can be carried out batch-wise or continuously.

The following Examples further illustrate the invention. Unless otherwise indicated, temperatures are in degrees Celsius and percentages are by weight. One bar pressure is 0.987 atmospheres.

EXAMPLE 1

A suspension of 133.3 g of triphenylphosphine dichloride and 9 g of 5 percent platinum-carbon in 1 liter of dry dioxan was hydrogenated in a glass flask with a steel stirrer at 50° and atmospheric pressure for 4 hours. The catalyst was filtered off and washed with dioxan. After evaporation of the filtrate, the residue was recrystallized from methanol. Yield 88.5 g (84.5%) of triphenylphosphine, m.p. 80°–81°. The mother liquor was recycled.

EXAMPLE 2

A suspension of 18.1 g of triphenylphosphine dichloride-chloroform adduct ($Ph_3PCl_2 \cdot CHCl_3$) and 0.5 g of palladium chloride in 100 ml of 1,2-dimethoxyethane was hydrogenated at 50° and 30 bar of hydrogen for 16 hours. Yield 8.6 g (81.8%) of triphenylphosphine.

EXAMPLE 3

205.4 g of triphenylphosphine dichloride-chloroform adduct in 1 liter of 1,2-dimethoxyethane were hydrogenated in a steel autoclave equipped with a stirrer in the presence of 10.5 g of platinum/palladium-carbon (1% Pt, 4% Pd) at 50° and 5 bar for 12 hours. Yield 96.3 g (81%) of triphenylphosphine.

EXAMPLE 4

A suspension of 18.1 g of triphenylphosphine dichloride-chloroform adduct and 0.9 g of 5 percent rhodium-carbon in 100 ml of 1,2-dimethoxyethane was hydrogenated at 50° and 30 bar of hydrogen for 12 hours. After filtration of the catalyst and distillation of the solvent, 8.51 g (81%) of triphenylphosphine were obtained by chromatography on silica gel.

EXAMPLE 5

18.1 g of triphenylphosphine dichloride-chloroform adduct were hydrogenated in the presence of 0.9 g of 5 percent ruthenium-carbon in 100 ml of chloroform at 125° and 30 bar of hydrogen for 3 hours. Yield 8.97 g (78%) of triphenylphosphine.

EXAMPLE 6

13.3 g of triphenylphosphine dichloride were hydrogenated with 0.9 g of 5 percent platinum-carbon in 100 ml of cyclohexane at 125° and 30 bar of hydrogen for 3 hours. Yield 9.0 g (86%) of triphenylphosphine.

EXAMPLE 7

181 g of triphenylphosphine dichloride-chloroform adduct were hydrogenated in the presence of 9 g of 5 percent iridium-carbon in 1 liter of chloroform at 125° and 30 bar of hydrogen for 3 hours. Yield 91.7 g (87.5%) of triphenylphosphine.

EXAMPLE 8

A suspension of 13.3 g of triphenylphosphine dichloride and 0.9 g of 5 percent platinum-carbon in 100 ml of toluene was hydrogenated at 125° and 5 bar hydrogen pressure for 2 hours. Yield 9.1 g (86.8%) of triphenylphosphine.

We claim:

1. A process for producing triphenylphosphine comprising hydrogenating triphenylphosphine dichloride in an inert solvent in the presence of a catalyst selected from the group consisting of platinum, palladium, rhodium, ruthenium and iridium.

2. The process of claim 1 wherein the inert solvent is an ether having at least 2 oxygen atoms.

3. The process of claim 2 wherein the ether is dioxane or 1,2-dialkoxyethane.

4. The process of claim 3 wherein the 1,2-dialkoxyethane is 1,2-dimethoxyethane.

5. The process of claim 1 wherein the inert solvent is chloroform, benzene, toluene, xylene, cyclohexane or ethyl acetate.

6. The process of claim 1 wherein the hydrogenation is carried out at a pressure of up to about 100 bar.

7. The process of claim 1 wherein the hydrogenation is carried out at a temperature of about 30° to about 130° C.

8. The process of claim 7 wherein the hydrogenation is carried out at a temperature of about 50° to about 60° C.

9. The process of claim 1 wherein the triphenylphosphine dichloride is used in the form of its chloroform adduct having the formula $(C_6H_5)_3PCl_2 \cdot CHCl_3$.

10. The process of claim 1 wherein the catalyst is used in an amount of up to about 5% by weight.

11. The process of claims 1 or 9 wherein the catalyst is ruthenium.

12. The process of claims 1 or 9 wherein the catalyst is platinum.

13. The process of claims 1 or 9 wherein the catalyst is iridium.

14. The process of claims 1 or 9 wherein the catalyst is rhodium.

15. The process of claims 1 or 9 wherein the catalyst is palladium.

16. The process of claims 1 or 9 wherein the catalyst is platinum and palladium.

17. A process for producing triphenylphosphine by hydrogenolysis of triphenylphosphine dichloride wherein the hydrogenolysis is carried out with hydrogen in the presence of a catalyst of platinum, palladium, rhodium, ruthenium or iridium.

18. A process for producing triphenylphosphine comprising hydrogenating a triphenylphosphine dichloride-chloroform adduct in an inert solvent in the presence of catalytic amounts of platinum, palladium, rhodium, ruthenium or iridium.

* * * * *